(12) United States Patent
Mundada et al.

(10) Patent No.: US 10,226,450 B2
(45) Date of Patent: Mar. 12, 2019

(54) PHARMACEUTICAL FILM COMPOSITION

(71) Applicants: SHILPA MEDICARE LIMITED, Rajendra Gunj, Raichur, Karnataka (IN); NU THERAPEUTICS PVT LTD, Cherlapally, Hyderabad, Telangana (IN)

(72) Inventors: Navneet Mundada, Hyderabad (IN); Ritesh Vinod Birla, Hyderabad (IN); Badrinath Allampalli, Raichur (IN); Akshay Kant Chaturvedi, Raichur (IN)

(73) Assignee: SHILPA MEDICARE LIMITED, Karnataka ( * ) Notice: Subject to any disclaimer, the term of this patent is extended or adjusted under 35 U.S.C. 154(b) by 0 days.

(21) Appl. No.: 15/512,575

(22) PCT Filed: Nov. 7, 2014

(86) PCT No.: PCT/IB2014/065871
§ 371 (c)(1),
(2) Date: Mar. 20, 2017

(87) PCT Pub. No.: WO2015/001541
PCT Pub. Date: Jan. 8, 2015

(65) Prior Publication Data
US 2017/0290807 A1  Oct. 12, 2017

(30) Foreign Application Priority Data
Sep. 25, 2014  (IN) .............. 4692/CHE/2014

(51) Int. Cl.
| | | |
|---|---|---|
| A01N 43/50 | (2006.01) |
| A61K 31/415 | (2006.01) |
| A61K 31/4178 | (2006.01) |
| A61K 9/00 | (2006.01) |
| A61K 47/32 | (2006.01) |
| A61K 9/70 | (2006.01) |
| A61K 47/10 | (2017.01) |
| A61K 47/26 | (2006.01) |
| A61K 47/38 | (2006.01) |
| A61K 47/36 | (2006.01) |

(52) U.S. Cl.
CPC .......... *A61K 31/4178* (2013.01); *A61K 9/006* (2013.01); *A61K 9/7007* (2013.01); *A61K 47/10* (2013.01); *A61K 47/26* (2013.01); *A61K 47/32* (2013.01); *A61K 47/36* (2013.01); *A61K 47/38* (2013.01)

(58) Field of Classification Search
None
See application file for complete search history.

(56) References Cited

U.S. PATENT DOCUMENTS

| | | |
|---|---|---|
| 8,580,830 B2 | 11/2013 | Leichs et al. |
| 2003/0053962 A1 | 3/2003 | Zerbe et al. |
| 2008/0213343 A1 | 9/2008 | Obermeier et al. |
| 2009/0017085 A1* | 1/2009 | Cilurzo ............ A61K 9/006 424/409 |
| 2010/0215774 A1* | 8/2010 | Maibach ........... A61K 9/0056 424/670 |
| 2010/0285130 A1* | 11/2010 | Sanghvi ............ A61K 9/006 424/484 |
| 2010/0297232 A1 | 11/2010 | Myers et al. |

FOREIGN PATENT DOCUMENTS

| | | |
|---|---|---|
| WO | 2005039543 A1 | 5/2005 |
| WO | 2006031209 A1 | 3/2006 |
| WO | 2008040534 A2 | 4/2008 |
| WO | 2012053006 A2 | 4/2012 |
| WO | 2003011259 A1 | 2/2013 |

\* cited by examiner

*Primary Examiner* — Jared Barsky

(57) ABSTRACT

The present invention relates to Film Compositions of Ondansetron or its pharmaceutically acceptable salt thereof, which dosage forms are useful for the treatment of various medical conditions.

1 Claim, No Drawings

PHARMACEUTICAL FILM COMPOSITION

FIELD OF THE INVENTION

The present invention relates to pharmaceutical film compositions of Ondansetron or its pharmaceutically acceptable salt thereof.

The invention also relates to process for preparing pharmaceutical film compositions, which dosage forms are comparable to immediate release solid oral dosage forms.

Said dosage forms may be useful for the treatment of various medical conditions.

BACKGROUND OF THE INVENTION

Ondansetron hydrochloride is a competitive serotonin 5-HT3 receptor antagonist used to prevent nausea and vomiting caused by cancer chemotherapy, radiation therapy, and surgery.

The chemical name of Ondansetron is (RS)-9-methyl-3-[(2-methyl-1H-imidazol-1-yl) methyl]-2,3-dihydro-1H-carbazol-4(9H)-one and its HCl salt is structurally represented as

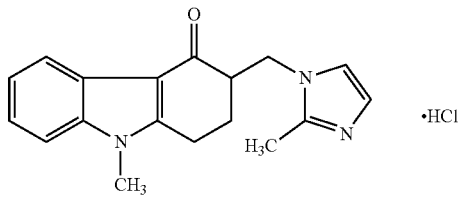 [SMILES: Cc1nccn1CC1CCc2c(c3ccccc3n2C)C1=O ; Cl]

Ondansetron hydrochloride is a white to off-white powder that is soluble in water and normal saline, having intensely bitter taste.

Ondansetron hydrochloride is commercially available as the conventional oral solid dosage forms in the strengths of 4 mg & 8 mg of ODT & 5 mL of ORAL SOLUTION is marketed with the Brand name ZOFRAN in the USA. 4-mg and 8-mg doses of either ZOFRAN oral solution or ZOFRAN ODT Orally disintegrating tablets are bioequivalent to corresponding dose of ZOFRAN tablets and may be used interchangeably.

Ondansetron hydrochloride films are commercially available as ZUPLENZ (ondansetron) oral soluble film approved in two strengths. The thin white opaque films are rectangularly shaped strips with a printed identifier in black ink of "4 mg" for ZUPLENZ 4 mg or "8 mg" for ZUPLENZ 8 mg. Each 8-mg ZUPLENZ oral soluble film for oral administration contains 8 mg ondansetron base. Each ZUPLENZ oral soluble film also contains the inactive ingredients butylated hydroxytoluene, calcium carbonate, colloidal silicon dioxide, erythritol, hydroxypropyl methylcellulose, monoammonium glycyrrhizinate, peppermint flavor, polyethylene oxide, sodium bicarbonate, sucralose, titanium dioxide and xanthan gum.

Christian et al in U.S. Pat. No. 8,580,830 provides a non-mucoadhesive orally disintegrating film dosage forms that mimic the pharmacokinetic profile of orally administered drug products such as tablets, capsules, liquid suspensions, and orally dissolving/dispersing tablet (ODT).

Christian et al provides a non-mucoadhesive orally disintegrating film comprising ondansetron or a pharmaceutically acceptable salt thereof in combination with a hydrophilic binder and a water-soluble diluent, able to disintegrate upon contact with saliva in the buccal cavity within about sixty seconds. Example 1 formulation comprise of ondansetron, polyvinylalcohol, polyethylene glycol, glycerol anhydrous, rice starch, acesulfame K, titanium dioxide, menthol and polysorbate.

Gary et al in US20100297232 relates to an ondansetron film compositions relating to a self-supporting film dosage composition comprising: a polymer mixture of PEO and HPMC, Xanthan gum as additive, an active component, at least one slow-dissolving alkaline component like calcium carbonate and at least one fast-dissolving alkaline component like sodium bicarbonate.

Robert et al in WO2006031209 relates to the film products and methods of their preparation that demonstrate a non-self-aggregating uniform heterogeneity. Desirably, these films disintegrate in water and may be formed by a controlled drying process, or other process that maintains the required uniformity of the film. The films contain a polymer component, which includes polyethylene oxide optionally blended with hydrophilic cellulosic polymers. These films also contain a pharmaceutical and/or cosmetic active agent with no more than a 10% variance of the active agent pharmaceutical and/or cosmetic active agent per unit area of the film. Robert et al. reference provides a rapid-dissolve film product comprising: at least one water-soluble polymer comprising polyethylene oxide alone or in combination with a hydrophilic cellulosic polymer, wherein said film product is free of added plasticizers.

Robert et al refers to a rapid-dissolve film product which is free of added plasticizers. The said prior art reference teaches different ratios of combination of polyethylene oxide with a hydrophilic cellulosic polymer, and use of surfactants and antifoaming agents as essential components for making film for achieving content uniformity of the pharmaceutical and/or cosmetic active agents in the film.

Horst et al in US20030053962 refers to a breath freshening film comprising: at least one hydroxypropyl cellulose; at least one modified starch; and at least one flavor ingredient. An improved rapidly disintegrating flavored film that quickly and completely disintegrates upon contact with mucosal tissue in the oral cavity of a human includes hydroxypropyl cellulose, a modified starch and a flavor ingredient. The flavored films of this invention completely disintegrate upon contact with the mucosal tissue in less than a minute, and often in less than 30 seconds, whereas previously known flavored films typically do not complete dissolve, or do not dissolve as rapidly, upon contact with mucosal tissue in the oral cavity of a human. The flavored films of this invention may be advantageously employed as breath freshening films, and in food items to impart flavor and, optionally, to impart functional qualities to the food item. However, these films do not provide a clean mouth sensation due to the fact that the hydrocolloids tend to gel on contact with saliva. One solution to the aforesaid drawbacks are provided in WO2003011259 from which is noted that, to obtain properties equivalent to those of pullulan, it is crucial that maltodextrin, smaller quantities of hydrocolloid and, additionally, inert filler are present simultaneously in the filmogenic composition.

Francesco et al in WO2005039543 relates to rapidly dissolving self-supporting films for food or pharmaceutical use comprising: a) a filmogenic substance consisting of a maltodextrin; b) a plasticiser; c) an active principle for food or pharmaceutical use, characterised in that said films are free of hydrocolloids.

Petra et al in US20080213343 relates to Film-form preparation comprising one or more film formers, one or more gel formers and one or more active ingredients selected from the group consisting of anti-emetics and anti-migraine agents, wherein said preparation is single-layered and are free of surfactants, effervescent additives and taste maskers.

Petra et al in US20080213343 relates to one or more film former(s) from the following group:

sugar, sugar alcohols and derivatives thereof, especially saccharose, sorbitol, mannitol, xylitol, glucose, fructose, lactose and galactose, low molecular weight organic acids, especially citric acid, succinic acid, malic acid and adipic acid, polyethylene glycol, polyethylene glycol dioleate, 1,3-butanediol, propylene glycol, glycerol, isopropyl palmitate, dibutyl sebacate, paraffin oil and castor oil, ethylcellulose, cellulose acetate, cellulose phthalate, and mixtures of such film formers.

Petra et al in US20080213343 relates to at least one gel former from the following group can be provided:

polymeric carbohydrates, especially cellulose and derivatives thereof, preferably hydroxypropylcellulose (HPC), hydroxypropylmethylcellulose (HPMC), starch and derivatives thereof, agar-agar, alginic acid, arabinogalactan, galactomannan, carrageenan, dextran, tragacanth and gum of vegetable origin, synthetic polymers that are soluble or swellable in water, especially polyvinylpyrrolidone, polyvinyl alcohol, polyacrylic acid and polyacrylamide, polypeptides, especially gelatin, albumin and collagen, and mixtures of such gel formers.

Rajesh et al in WO2012/053006 relates to an oral fast dispersing or dissolving film for delivery of active comprising therapeutically effective amount of an active pharmaceutical agent, at least one water soluble polymer as essential polymer base in combination with film forming polymer in a ratio of about 25:1 to about 250:1. The prior art reference discloses an oral fast dispersing or dissolving film comprising a. about 2-40% of ondansetron, b. about 0.1-2% of pectin, c. about 10-50% of hydroxypropyl methyl cellulose and d. about 10-50% of maltodextrin.

Each of the films of the representative prior art patents, discussed briefly above have certain disadvantages as compared to the components of the films and methods of the present invention. The following disadvantages can be observed like— a) Robert et al refers to a rapid-dissolve film product made of polyethylene oxide with a hydrophilic cellulosic polymer which is free of added plasticizers. However, the use of surfactants and antifoaming agents were inevitable components for making films.

b) Petra et al in US20080213343 relates to Antiemetic Film preparations comprising one or more film formers, one or more gel formers wherein said preparation is single-layered and are free of taste maskers. The undesired taste of the drug would be unacceptable and may not provide patient compliance.

c) Francesco et al in WO2005039543 relates to rapidly dissolving self-supporting films for food or pharmaceutical use comprising: a) a filmogenic substance consisting of a maltodextrin; b) a plasticiser; c) an active principle for food or pharmaceutical use, characterised in that said films are free of hydrocolloids. The high concentrations of maltodextrin can pose problems in making film preparations.

d) Gary et al in US20100297232 relates to an ondansetron film compositions relating to a self-supporting film dosage composition comprising: a polymer mixture of PEO and HPMC, Xanthan gum, calcium carbonate and sodium bicarbonate. The presence of slow-dissolving alkaline component like calcium carbonate and fast-dissolving alkaline component like sodium bicarbonate and also pose several formulation challenges in film preparation and would greatly affect the product characteristics.

Despite the wide existence of teachings for making ondansetron oral films in the prior art, however, still there is a need for providing an economically feasible, improved, stable oral film that is easy to make and that can accommodate drugs like ondansetron.

Surprisingly, an improved pharmaceutical Film Compositions of Ondansetron or a salt thereof, methods of formulating the Film Compositions of Ondansetron or a salt thereof, and are comparable to commercially available Ondansetron solid oral dosage foal's.

SUMMARY OF THE INVENTION

Aspects of the present invention relates to a pharmaceutical film composition comprising:

a) Ondansetron or its pharmaceutically acceptable salt thereof;

b) water-soluble polymer mixture consisting essentially of combination of hydrophillic cellulosic polymers, maltodextrin and polyethylene oxide;

c) a plasticizer;

d) at least any one of the excipients selected from Colorants, flavouring agents, sweeteners and ion-exchange resins.

Aspects of the present invention relates to a process of preparing pharmaceutical film composition comprising:

a) Ondansetron or its pharmaceutically acceptable salt thereof;

b) water-soluble polymer mixture consisting essentially of combination of hydrophillic cellulosic polymers, maltodextrin and polyethylene oxide;

c) a plasticizer;

d) at least any one of the excipients selected from Colorants, flavouring agents, sweeteners and ion-exchange resins.

Aspects of the present invention relates to a pharmaceutical film composition comprising Ondansetron or its pharmaceutically acceptable salt thereof, wherein film having a surface area of greater than 7 cm$^2$.

Abbreviations

| | |
|---|---|
| RPM | Rotations Per Minute |
| API | Active Pharmaceutical Ingredient |
| NLT | Not less than |
| PEO | Polyethylene oxide |
| HPMC | Hydroxypropyl methyl cellulose |
| ODF | Orally dissolving films |
| % w/w | Percent weight by weight |

DETAILED DESCRIPTION

As set forth in our endeavor to the present invention, it describes a pharmaceutical film composition of Ondansetron or its pharmaceutically acceptable salts, which is suitable for the treatment of various medical conditions like— a) prevention of nausea and vomiting associated with highly emetogenic cancer chemotherapy;
b) prevention of nausea and vomiting associated with initial and repeat courses of moderately emetogenic cancer chemotherapy treatment or disorder related to emesis;
c) prevention of nausea and vomiting associated with radiotherapy in patients receiving total body irradiation, single high-dose fraction to abdomen, or daily fractions to the abdomen;
d) prevention of postoperative nausea and/or vomiting.

In one embodiment according to the present invention, it provides a method of treating or preventing emesis in a human patient comprising administering to the tongue of said patient, preferably from one to three times daily, an ondansetron film of the present invention that contains from about 4 to about 24 mg of ondansetron base, preferably 4 or 8 mg of ondansetron base. The method of administration can be with or without water.

In one embodiment according to the present invention, it provides a pharmaceutical film composition of Ondansetron or its pharmaceutically acceptable salts comprising:
a) Ondansetron or its pharmaceutically acceptable salt thereof;
b) water-soluble polymer mixture consisting essentially of combination of hydrophillic cellulosic polymers, maltodextrin and polyethylene oxide;
c) a plasticizer;
d) at least any one of the excipients selected from Colorants, flavouring agents, sweeteners and ion-exchange resins.

The pharmaceutical film composition used in the context of the present application refers to edible dosage forms suitable for administration of a drug by oral route. An advantage for these dosage forms, when compared to tablets, capsules and other dosage forms that must be swallowed, is that some patient populations have difficulty swallowing, such as children and the elderly.

In the above embodiment the drug ondansetron or a pharmaceutically acceptable salt may be selected from Ondansetron base or its salts like Ondansetron hydrochloride or other similar salt.

In one of the particular embodiment of the pharmaceutical film composition, Ondansetron hydrochloride salt was taken for preparing the same.

The hydrophillic cellulosic polymers that are used in the above embodiment of the present invention are selected from hydroxypropyl methyl cellulose and hydroxy propyl cellulose. These polymeric materials are freely soluble in aqueous medium and provides the basic component for the film formation. These excipients may be used in the present composition upto about 20% to about 50% w/w of the total film composition.

In one of the particular embodiment of the pharmaceutical film composition, hydrophillic cellulosic polymers used is hydroxypropyl methyl cellulose for preparing the same. Said hydrophillic cellulosic polymers was utilized preferably upto 25 w/w of the total film composition.

The Maltodextrin which is used in the above embodiment of the present invention is another polymeric material, is freely soluble in aqueous medium and provides second major contribution to the film composition. These may be used in the present composition between about 10% w/w to about 20% w/w of the film composition.

The maltodextrin which is used in the above embodiment of the present invention is another polymeric material, is freely soluble in aqueous medium and provides integrity in the film composition. These may be used in the present composition below 15% w/w of the total film composition.

In one of the embodiment of the pharmaceutical film composition, polyethylene oxide utilized preferably, is between 2-15% w/w of the total film composition.

Usually plasticizer significantly improves the strip properties by reducing the glass transition temperature of the polymer. Typically the plasticizers are used in the concentration of 1-20% w/w of dry polymer weight. Examples include: Glycerol, Propylene glycol, Low molecular weight polyethylene glycols, Citrate derivatives like triacetin, acetyl citrate, Phthalate derivatives like dimethyl, diethyl, dibutyl derivatives, Castor oil etc. In the above embodiment the plasticizer used for the pharmaceutical film composition is selected from glycerol and propylene glycol, which are freely soluble in aqueous medium and provide good elasticity to the polymeric film. The plasticizer utilized preferably between 5-20% w/w of the total film composition depending on the individual % w/w concentrations of hydrophillic cellulosic polymers, maltodextrin and polyethylene oxide respectively.

In one of the particular embodiment of the pharmaceutical film composition, glycerol was taken for preparing the same. The preferred range of plasticizer is between 5-15% w/w of the total film composition.

Another embodiment of the present invention it provides a process for preparing a pharmaceutical film composition of Ondansetron comprising the steps of—
a. Providing a solution of Ondansetron hydrochloride in purified water,
b. Adding Ion exchange resins and sweeteners into step (a) solution followed by Polyethylene oxide addition;
c. Add Maltodextrin into step (b) solution;
d. Optionally adding flavours into step (c) solution;
e. Preparing separately an aqueous dispersion of hydrophillic cellulosic polymers;
f. Transferring the dispersion of step (e) into step (d) solution;
g. Homogenizing the solution in step (f);
h. Adding plasticizers into step (g) solution, followed by dispersing colors and flavours;
i. Obtaining the film composition onto a polyester film.

The individual steps of the process are detailed herein below—

Step-a: Providing a Solution of Ondansetron Hydrochloride in Purified Water—

Step of providing a solution of Ondansetron hydrochloride in purified water comprise adding slowly Ondansetron or its pharmaceutically acceptable salt like hydrochloride salt in purified water in a formulation tank under high stirring (bottom stirring) at speed of about 400-600 RPM for suitable time to achieve the complete dissolution. In one of the embodiment, Ondansetron hydrochloride is found to be dissolved in water within 5 minutes.

Step-b: Adding Ion Exchange Resins and Sweeteners into Step (a) Solution Followed by Polyethylene Oxide Addition—

Step of adding Ion exchange resins into step (a) solution. Usually the stirring speed (bottom stirring) at speed of 1000±100 RPM for appropriate time and stirring time is below 5 minutes.

Suitable ion exchange resins are described particularly in U.S. Pat. No. 7,067,116 to Bess et al. Preferred ion exchange resins are water-insoluble and consist of a pharmacologically inert organic or inorganic matrix containing covalently bound functional groups that are ionic or capable of being ionized under the appropriate conditions of pH. The organic matrix may be synthetic (e.g., polymers or copolymers of acrylic acid, methacrylic acid, sulfonated styrene, sulfonated divinylbenzene), for eg. Polacraline potassium, or partially synthetic (e.g., modified cellulose and dextrans). The inorganic matrix can also be, e.g., silica gel modified by the addition of ionic groups. The covalently bound ionic groups may be strongly acidic (e.g., sulfonic acid), weakly acidic (e.g., carboxylic acid), strongly basic (e.g., quaternary ammonium), weakly basic (e.g., primary amine), or a combination of acidic and basic groups. In general, those types of ion exchangers suitable for use in ion exchange chromatography and for such applications as deionization of water are suitable for use in these controlled release drug preparations.

According to present invention the ion exchange resins also exhibit taste masking agent and mask the unpleasant taste of ondansetron or its salt.

After addition of ion exchange resins, start anchoring at 50-70 RPM, especially 60 RPM is preferred speed, and followed by adding and dissolving sweeteners into above solution. The addition of sweeteners to be carried at anchor speed followed by high speed stirring of about 1000 RPM is required for 1 minute.

Suitable sweeteners that can be included are those well known in the art, including both natural and artificial sweeteners.

Suitable sweeteners include, e.g.:

A. water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin;

B. water-soluble artificial sweeteners such as sucralose or the soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like;

C. dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2, 2, 4, 4-tetramethyl-3-thietanyl)-D-alaninamide hydrate, methyl esters of L-aspartyl-L-phenylglycerin and L-aspartyl-L-2, 5, dihydrophenyl-glycine, L-aspartyl-2, 5-dihydro-L-phenylalanine, L-aspartyl-L-(1-cyclohexyen)-alanine, and the like;

D. water-soluble sweeteners derived from naturally occurring water-soluble sweeteners, such as a chlorinated derivative of ordinary sugar (sucrose), known, for example, under the product description of sucralose; and E. protein based sweeteners such as thaumatoccous danielli (Thaumatin I and II).

After addition of sweeteners, add slowly Polyethylene oxide while continuing anchoring for about 1-2 minutes at 60±5 RPM followed by high speed stirring at 1000±100 RPM.

Step-(c): Add Maltodextrin into Step (b) Solution—

Adding slowly Maltodextrin into step-(b) solution while continuing anchoring for about 1-2 minutes at 60±5 RPM followed by high speed stirring at 1000±100 RPM.

Step-(d): Optionally Adding Flavours into Step (c) Solution—

Optionally adding flavours into step-(c) solution while continue anchoring for about 1-2 minutes at 60±5 RPM followed by high speed stirring at 1000±100 RPM, for appropriate time, stop stirring and keep the formulation aside.

The flavours that can be used include those known to the skilled artisan, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, banana, chocolate, coffee, cocoa and citrus oil, including lemon, orange, grape, lime and grapefruit and fruit essences including apple, pear, peach, strawberry, raspberry, cherry, plum, pineapple, apricot and so forth. These flavorings can be used individually or in admixture. Commonly used flavors include mints such as peppermint, artificial vanilla, cinnamon derivatives, and various fruit flavors, whether employed individually or in admixture. Flavorings such as aldehydes and esters including cinnamyl acetate, cinnamaldehyde, citral, diethylacetal, dihydrocarvyl acetate, eugenyl formate, p-methylanisole, and so forth may also be used. Generally, any flavoring or food additive, such as those described in Chemicals Used in Food Processing, publication 1274 by the National Academy of Sciences, pages 63 258, may be used. Further examples of aldehyde flavorings include, but are not limited to acetaldehyde (apple); benzaldehyde (cherry, almond); cinnamic aldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. melonal (melon); 2-6-dimethyloctanal (green fruit); and 2-dodecenal (citrus, mandarin); cherry; grape; mixtures thereof; and the like.

Step-(e): Preparing Separately an Aqueous Dispersion of Hydrophillic Cellulosic Polymers—

Separately preparing a dispersion of hydrophillic cellulosic polymers in purified water at a temperature of 70° C. to 85° C., preferably at 80° C.±2° C. and the stirring speed of about 50±5 RPM. Usually, uniform dispersion can be obtained after stirring for 20-40 minutes.

Step-(f): Transferring the Dispersion of Step (e) into Step (d) Solution;

Slowly transferring the polymer dispersion of step (e) into Formulation tank of step (d) under stirring for 20-40 minutes, preferably about 30 minutes with high speed stirrer at 2000±100 RPM and anchor blade 40±5 RPM.

Step-(g): Homogenizing the Solution in Step (f)—

Homogenizing the solution formulation obtained in step (f) and optionally de-aeration of the formulation for about 30±5 minutes.

Step-(h): Adding Plasticizers into Step (g) Solution, Followed by Dispersing Colors and Flavours—

Slowly add and dissolve plasticizers into step (g) solution with anchor blade speed of 60±5 RPM and start homogenization for about 10-15 minutes.

Disperse colours into solution under stirring with anchor blade speed of 60±5 RPM and start homogenization for about 10-15 minutes, and then added additional flavours under homogenization and start anchoring at 60±5 RPM for about 10-15 minutes.

The colours useful in the present invention include pigments such as titanium dioxide, which may be incorporated in amounts of up to about 5 wt %, and preferably less than about 1 wt %. Colorants can also include natural food colors and dyes suitable for food, drug and cosmetic applications. These colorants are known as FD&C dyes and lakes. The materials acceptable for the foregoing spectrum of use are preferably water-soluble, and include Carmosine, FD&C Blue No. 2, which is the disodium salt of 5,5-indigotindisulfonic acid. Similarly, the dye known as Green No. 3 comprises a triphenylmethane dye and is the monosodium salt of 4-[4-N-ethyl-p-sulfobenzylamino) diphenyl-methylene]-[1-N-ethyl-N-p-sulfonium benzyl)-2,5-cyclo-hexadienimine]. A full recitation of all FD&C and D&C dyes and their corresponding chemical structures may be found in the Kirk-Othmer Encyclopedia of Chemical Technology, Volume 5, Pages 857-884, which text is accordingly incorporated herein by reference.

Step-(i): Obtaining the Film Composition onto a Polyester Film—

After the addition of colours and additional flavours, the stirring operation can be continued for few hours for few hours eg. 4-10 hours. The final De-aeration step of dispersion can be carried out for every 45±5 minutes for 10±5 minutes at pressure (600 to 750 mm Hg).

Cooled water circulation 10° C. to 20° C., preferably 15° C.±5° C. through the jacket of the formulation tank throughout the homogenization and deaeration process to maintain formulation temperature at 25° C.-30° C.

Fix the bi-axially oriented transparent polyester film of food grade for eg. J-200 of Jindal make at unwinding junction. Keep the formulation dispersion under stirring with anchor blade at 5 RPM while layering and drying. The drying step can be carried out by employing dryer temperature at 80° C.-100° C. for appropriate time, preferably few minutes for e.g. below 10 minutes.

Primary Packing:

The slitted roll is then placed in packing machine where the product is cut into desired length and breadth, and packed in triple laminate aluminium pouch.

The desired weight range of Ondansetron strips according to the present invention is between 40 mg to 100 mg, preferably, around 40 mg-45 mg for Ondansetron strips 4 mg and 60 mg-65 mg for Ondansetron strips 8 mg.

The desired size range of Ondansetron strips according to the present invention is the following: 32×32 mm for Ondansetron strips 8 mg and 32×25 mm for Ondansetron strips 4 mg.

In one of the embodiments of the present invention, it provides a pharmaceutical film composition comprising Ondansetron or its pharmaceutically acceptable salt thereof, wherein film having a surface area of greater than 7 $cm^2$. Preferably, about 8 $cm^2$ for Ondansetron strips 4 mg and about 10 $cm^2$ for Ondansetron strips 8 mg respectively.

In one of the particular embodiments of the present invention, provides a pharmaceutical film composition comprising: Ondansetron hydrochloride, Hydroxypropyl methyl cellulose, Maltodextrin, Polyethylene oxide, Glycerol, Polacriline potassium resin, Sucralose, Carmoisine colour, Vanilla and Banana flavours.

The invention also provides various methods of treatment, based on the particular active agent involved, that rely on one or more of several defining characteristics, including the placement of the dosage form on the tongue, swallowing the dosage form within ten, twenty, thirty, forty-five or sixty seconds, and swallowing the dosage form with or without water.

In one of the embodiments of the present invention, the film dispersion time of pharmaceutical film composition is rapid within ten seconds and the disintegration time of the invention pharmaceutical film compositions can be determined according to the disintegration test <701> of Ondansetron Orally disintegration tablets USP.

Usually the film disintegration time of the invention pharmaceutical film compositions is not more than 1 minute, preferably less than 30 seconds and most preferably less than 10 seconds.

In one of the embodiments of the present invention, the dissolution time of the invention pharmaceutical film composition can be determined according to the dissolution test <711> of Ondansetron Orally disintegration tablets USP.

Usually the drug dissolution time from the invention pharmaceutical film compositions is NLT 80% of drug gets dissolved in 10 minutes.

In one of the embodiments of the present invention, the dissolution time of the invention pharmaceutical film composition are comparable to ZUPLENZ (ondansetron) oral soluble film & ZOFRAN ODT.

The example given below serve to illustrate embodiments of the present invention. However, they do not intend to limit the scope of present invention.

Example 1

Preparation of Ondansetron Hydrochloride Film Composition—Equivalent to Ondansetron 8 mg:

A film formulation was prepared with the following components:

TABLE 1

| Ingredients | Wt in mg/Strip | Composition Per Unit (%) |
| --- | --- | --- |
| Ondansetron hydrochloride | 9.99 | 15.45 |
| Polacriline potassium resin | 5.70 | 8.82 |
| Sucralose | 5.66 | 8.75 |
| Maltodextrin | 8.40 | 12.99 |
| Polyethylene Oxide | 5.43 | 8.40 |
| Hydroxypropylmethylcellulose | 13.98 | 21.62 |
| Glycerol | 8.52 | 13.18 |
| Carmoisine | 0.02 | 0.03 |
| Vanilla | 1.97 | 3.05 |
| Banana | 4.99 | 7.71 |
| Purified Water | Q.S | Q.S |
| Total weight of dosage form | 64.66 | 100 |

The process of preparation of pharmaceutical film of Ondansetron or salt thereof comprising the following steps:
1. Purified water was taken, and Ondansetron hydrochloride was added with continuous stirring with 500±100 RPM for 3±1 min.
2. Polacriline potassium was added to the contents of step 1 and stirred for 2 min at 1000±100 RPM.
3. Sucralose was added to the contents of step 2 and during addition of sweetener anchoring continued for about 1-2 minutes at 60±5 RPM followed by high speed stirring at 1000±100 RPM.
4. Polyethylene oxide was added to the contents of step 3 and during addition of PEO anchoring continued for about 1-2 minutes at 60±5 RPM followed by high speed stirring at 1000±100 RPM.

5. Maltodextrin was added to the contents of step 4 while continuing anchoring for about 1-2 minutes at 60±5 RPM followed by high speed stirring at 1000±100 RPM.
6. Vanilla flavour was added to the contents of step 5 while continuing anchoring for about 1-2 minutes at 60±5 RPM followed by high speed stirring at 1000±100 RPM.
7. Separately preparing a dispersion of HPMC in purified water at a temperature of 80° C.±5° C. and the stirring speed of about 50±5 RPM. Usually, uniform dispersion obtained after stirring for about 30 minutes.
8. Hydroxypropylmethylcellulose dispersion of step 7 was added to the above contents of step 6 and stirring continued at 2000±100 RPM for 30±2 min and anchor blade 40±5 RPM.
9. Homogenize the above dispersion and de-aerate the formulation for 10±5 min at 600 to 735 mmHg with anchor blade stirring at 50±5 RPM.
10. Glycerol was added to the contents of the homogenized formulation with anchor blade stirring at 60±5 RPM for 10±2 min.
11. Carmoisine was dispersed to the above homogenized formulation with anchor blade stirring at 60±5 RPM and homogenization continued with anchoring for about 10 minutes.
12. After addition of colours (carmoisine) and banana flavors to the above homogenized dispersion formulation with anchor blade stirring at 60±5 RPM and the process continued for 4 hours.
13. After the addition of colours and additional flavours, the stirring operation can be continued for four hours. The final De-aeration step of step-12 dispersion can be carried out for every 45±5 minutes for 10±5 minutes at pressure (600 to 750 mm Hg). Cooled water circulation 10° C. to 20° C., preferably 15° C.±5° C. through the jacket of the formulation tank throughout the homogenization and deaeration process to maintain formulation temperature at 25° C.-30° C.
14. Fix the bi-axially oriented transparent polyester film J-200 of Jindal make at unwinding junction. The formulation dispersion kept under stirring with anchor blade at 5 RPM while layering and drying. The drying step can be carried out by employing dryer temperature at 80° C.-100° C. for appropriate time, preferably few minutes for below 10 minutes.

Packing:

The slitted roll of 32 mm width is then placed in packing machine where the product is again cuts to 32 mm and packed in triple laminate aluminium pouch.

Physical Parameters of the Strips:

Strip appearance:—Good.

Strip peelability:—Good.

Strip strength:—Good.

180° bending:—Good.

Disintegration time for six units of Example 1 Ondasnetron 8 mg ODF is between 5-10 seconds.

Strip Size:—32×32 mm (1024 mm² surface area).

Strip weight range: 64.50 mg-64.80 mg

Strip thickness: 500µ

Dissolution profile comparison of Vomikind MD 8 mg (Commercially available Ondansetron mouth dissolving tablet) against Example 1 Ondasnetron 8 mg ODF (Media: pH 1.2):

TABLE 2

| Batch No | Tablet | 5 min | 10 min | 15 min | 20 min | 30 min |
| --- | --- | --- | --- | --- | --- | --- |
| Reference: | Tab-1 | 82.3 | 97.50 | 101.4 | 102.8 | 102.8 |
| Vomikind | Tab-2 | 79.1 | 96.1 | 101.3 | 102.6 | 103.0 |
| MD - 8 mg | Tab-3 | 82.7 | 99.7 | 102.3 | 103.3 | 103.2 |
| | Tab-4 | 82.3 | 98.3 | 101.7 | 102.2 | 102.7 |
| | Tab-5 | 80.8 | 96.6 | 99.3 | 101.0 | 101.5 |
| | Tab-6 | 83.7 | 100.9 | 103.2 | 103.4 | 103.9 |
| | Tab-7 | 80.7 | 97.7 | 101.6 | 102.7 | 102.9 |
| | Tab-8 | 80.0 | 96.4 | 100.9 | 102.8 | 103.2 |
| | Tab-9 | 82.7 | 99.0 | 102.2 | 103.5 | 103.5 |
| | Tab-10 | 81.7 | 98.8 | 101.5 | 102.3 | 102.9 |
| | Tab-11 | 83.0 | 97.0 | 100.2 | 101.9 | 102.2 |
| | Tab-12 | 82.3 | 99.3 | 102.7 | 103.2 | 103.7 |
| | Average | 81.7 | 98.1 | 101.5 | 102.6 | 102.9 |
| Example 1 | Film-1 | 82.6 | 96.9 | 99.7 | 100.3 | 101.0 |
| Ondansetron | Film-2 | 81.6 | 97.5 | 100.0 | 100.8 | 101.3 |
| ODF - 8 mg | Film-3 | 81.8 | 97.5 | 100.3 | 100.9 | 100.9 |
| | Film-4 | 82.1 | 98.0 | 100.2 | 100.8 | 101.0 |
| | Film-5 | 81.5 | 98.3 | 100.5 | 100.8 | 101.0 |
| | Film-6 | 81.8 | 98.7 | 100.6 | 100.9 | 101.2 |
| | Film-7 | 81.6 | 97.0 | 99.6 | 100.7 | 100.8 |
| | Film-8 | 82.2 | 97.4 | 99.4 | 100.8 | 100.9 |
| | Film-9 | 82.3 | 98.1 | 99.9 | 100.6 | 100.8 |
| | Film-10 | 81.9 | 98.3 | 99.9 | 100.6 | 100.4 |
| | Film-11 | 82.2 | 98.3 | 100.0 | 100.7 | 101.5 |
| | Film-12 | 82.0 | 98.7 | 100.7 | 100.6 | 101.0 |
| | Average | 81.9 | 97.9 | 100.1 | 100.7 | 101.0 |

Example 2

Preparation of Ondansetron Hydrochloride Film Composition—Equivalent to Ondansetron 4 mg:

A film formulation was prepared with the following components:

TABLE 3

| Ingredients | Wt in mg/Strip | Composition Per Unit (%) |
| --- | --- | --- |
| Ondansetron hydrochloride | 4.99 | 11.82 |
| Polacriline potassium resin | 2.99 | 7.08 |
| Sucralose | 3.61 | 8.55 |
| Maltodextrin | 7.23 | 17.13 |
| Polyethylene Oxide | 2.17 | 5.14 |
| Hydroxypropylmethylcellulose | 13.01 | 30.82 |
| Glycerol | 3.65 | 8.65 |
| Carmoisine | 0.015 | 0.04 |
| Vanilla | 1.525 | 3.61 |
| Banana | 3.02 | 7.15 |
| Purified Water | Q.S | Q.S |
| Total weight of dosage form | 42.21 | 100 |

The process of preparation of pharmaceutical film of Ondansetron or salt thereof comprising the following steps:
1. Purified water was taken, and Ondansetron hydrochloride was added with continuous stirring with 500±100 RPM for 3±1 min.
2. Polacriline potassium was added to the contents of step 1 and stirred for 2 min at 1000±100 RPM.
3. Sucralose was added to the contents of step 2 and during addition of sweetener anchoring continued for about 1-2 minutes at 60±5 RPM followed by high speed stirring at 1000±100 RPM.
4. Polyethylene oxide was added to the contents of step 3 and during addition of PEO anchoring continued for about 1-2 minutes at 60±5 RPM followed by high speed stirring at 1000±100 RPM.
5. Maltodextrin was added to the contents of step 4 while continuing anchoring for about 1-2 minutes at 60±5 RPM followed by high speed stirring at 1000±100 RPM.

6. Vanilla flavour was added to the contents of step 5 while continuing anchoring for about 1-2 minutes at 60±5 RPM followed by high speed stirring at 1000±100 RPM.
7. Separately preparing a dispersion of HPMC in purified water at a temperature of 80° C.±5° C. and the stirring speed of about 50±5 RPM. Usually, uniform dispersion obtained after stirring for about 30 minutes.
8. Hydroxypropylmethylcellulose dispersion of step 7 was added to the above contents of step 6 and stirring continued at 2000±100 RPM for 30±2 min and anchor blade 40±5 RPM.
9. Homogenize the above dispersion and de-aerate the formulation for 10±5 min at 600 to 735 mmHg with anchor blade stirring at 50±5 RPM.
10. Glycerol was added to the contents of the homogenized formulation with anchor blade stirring at 60±5 RPM for 10±2 min.
11. Carmoisine was dispersed to the above homogenized formulation with anchor blade stirring at 60±5 RPM and homogenization continued with anchoring for about 10 minutes.
12. After addition of colours (carmoisine) and banana flavors to the above homogenized dispersion formulation with anchor blade stirring at 60±5 RPM and the process continued for 4 hours.
13. After the addition of colours and additional flavours, the stirring operation can be continued for four hours. The final De-aeration step of step-12 dispersion can be carried out for every 45±5 minutes for 10±5 minutes at pressure (600 to 750 mm Hg). Cooled water circulation 10° C. to 20° C., preferably 15° C.±5° C. through the jacket of the formulation tank throughout the homogenization and deaeration process to maintain formulation temperature at 25° C.-30° C.
14. Fix the bi-axially oriented transparent polyester film J-200 of Jindal make at unwinding junction. The formulation dispersion kept under stirring with anchor blade at 5 RPM while layering and drying. The drying step can be carried out by employing dryer temperature at 80° C.-100° C. for appropriate time, preferably few minutes for below 10 minutes.

Packing:

The slitted roll of 32 mm width is then placed in packing machine where the product is again cuts to 25 mm and packed in triple laminate aluminium pouch.

Physical Parameters of the Strips:
Strip appearance:—Good.
Strip peelability:—Good.
Strip strength:—Good.
180° bending:—Good.

Disintegration time for six units of Example 2 Ondasnetron 4 mg ODF is between 5-10 seconds.

Strip Size:—32×25 mm (800 mm$^2$ surface area).
Strip weight range: 42.1 mg-42.8 mg
Strip thickness: 510μ

Dissolution profile comparison of Vomikind MD 4 mg (Commercially available Ondansetron mouth dissolving tablet) against Example 2 Ondasnetron 4 mg ODF (Media: pH 1.2):

TABLE 4

| Batch No | Tablet | 5 min | 10 min | 15 min | 20 min | 30 min |
|---|---|---|---|---|---|---|
| Reference: | Tab-1 | 78.6 | 99.2 | 102.3 | 194.4 | 104.4 |
| Vomikind | Tab-2 | 69.7 | 88.0 | 96.9 | 99.5 | 101.6 |
| MD - 4 mg | Tab-3 | 82.1 | 99.5 | 101.3 | 101.8 | 102.7 |
|  | Tab-4 | 79.8 | 86.2 | 102.7 | 103.9 | 103.7 |
|  | Tab-5 | 97.4 | 100.4 | 101.3 | 101.8 | 101.6 |
|  | Tab-6 | 89.8 | 102.3 | 104.1 | 104.8 | 105.1 |
|  | Tab-7 | 95.3 | 105.3 | 107.4 | 107.6 | 109.0 |
|  | Tab-8 | 78.7 | 92.7 | 101.6 | 106.0 | 109.5 |
|  | Tab-9 | 89.0 | 105.1 | 105.5 | 107.2 | 107.6 |
|  | Tab-10 | 97.8 | 106.2 | 106.7 | 108.1 | 109.7 |
|  | Tab-11 | 98.1 | 109.3 | 110.2 | 110.0 | 112.5 |
|  | Tab-12 | 91.3 | 107.8 | 108.1 | 109.3 | 112.8 |
|  | Average | 87.3 | 101.0 | 104.0 | 105.4 | 106.7 |
| Example 2 | Film-1 | 88.4 | 104.6 | 105.1 | 106.9 | 106.9 |
| Ondansetron | Film-2 | 87.7 | 104.8 | 106.5 | 104.6 | 105.1 |
| ODF - 4 mg | Film-3 | 86.5 | 104.1 | 105.5 | 105.3 | 102.3 |
|  | Film-4 | 85.1 | 103.2 | 106.2 | 104.6 | 106.7 |
|  | Film-5 | 84.7 | 102.7 | 103.9 | 105.1 | 105.8 |
|  | Film-6 | 86.7 | 102.3 | 103.9 | 106.0 | 105.8 |
|  | Film-7 | 85.2 | 103.9 | 104.8 | 105.5 | 106.9 |
|  | Film-8 | 85.6 | 103.7 | 105.8 | 105.5 | 104.1 |
|  | Film-9 | 86.1 | 101.4 | 104.4 | 105.5 | 105.6 |
|  | Film-10 | 86.5 | 101.6 | 104.8 | 104.4 | 105.6 |
|  | Film-11 | 87.0 | 101.8 | 102.7 | 104.1 | 105.1 |
|  | Film-12 | 86.1 | 102.7 | 103.7 | 103.9 | 104.8 |
|  | Average | 86.3 | 103.1 | 104.8 | 105.1 | 105.4 |

The invention claimed is:

1. A pharmaceutical film composition consisting of:
a) 11.0% w/w to 16.0% w/w ondansetron hydrochloride based on total weight of film composition;
b) water-soluble polymer mixture consisting of 21.0% w/w to 31.0% w/w hydroxypropyl methylcellulose, 12.5% w/w to 18.0% w/w maltodextrin and 5.1% w/w to 9.0% w/w polyethylene oxide based on the total weight of the film composition;
c) 8.5% w/w to 14.0% w/w glycerin based on total weight of film composition;
d) 7.0% w/w to 9.0% w/w polacrilin potassium based on total weight of film composition; and
e) at least one excipient selected from colorants, flavouring agents and sweeteners; wherein the film surface area is 8 cm$^2$ to 10 cm$^2$.

* * * * *